United States Patent [19]

Felix et al.

[11] Patent Number: 4,851,597
[45] Date of Patent: Jul. 25, 1989

[54] PROCESS FOR THE THERMAL CLEAVAGE OF 1,2-DICHLOROETHANE

[75] Inventors: Bernd Felix; Walter Fröhlich, both of Burgkirchen; Heiner Katzenberger, Burghausen, all of Fed. Rep. of Germany

[73] Assignee: Hochst Aktiengesellschaft, Frankfurt am Main, Fed. Rep. of Germany

[21] Appl. No.: 637,895

[22] Filed: Aug. 6, 1984

[30] Foreign Application Priority Data

Aug. 9, 1983 [DE] Fed. Rep. of Germany ....... 3328691

[51] Int. Cl.$^4$ ............................................. C07C 17/34
[52] U.S. Cl. .................................................... 570/227
[58] Field of Search ................................ 570/227, 226

[56] References Cited

U.S. PATENT DOCUMENTS 2,447,410  8/1948  Hampel .............................. 570/218
2,755,315  7/1956  Eberly ................................. 570/227

FOREIGN PATENT DOCUMENTS 19813  10/1967  Japan ................................... 570/226

Primary Examiner—Howard T. Mars
Attorney, Agent, or Firm—Curtis, Morris & Safford

[57] ABSTRACT

A process for the thermal cleavage of 1,2-dichloroethane to give vinyl chloride at 300° to 600° C. under atmospheric pressure or elevated pressure is described. Before cleavage of the 1,2-dichloroethane, 0.001 to 5% by weight of trichloroacetyl chloride or a compound which contains 3 carbon atoms, at least 6 chlorine atoms, 0 to 1 oxygen atom and, for each carbon atom bonded to the latter, 0 or 1 hydrogen atom, is added to it. Due to the addition of the compound(s) mentioned, the conversion is increased at the same cleavage temperature, or the cleavage temperature is reduced at the same conversion, at the same time a reduction in interfering byproducts being observed.

3 Claims, No Drawings

PROCESS FOR THE THERMAL CLEAVAGE OF 1,2-DICHLOROETHANE

The invention relates to a process for the thermal cleavage of 1,2-dichloroethane in the presence of certain compounds which accelerate the cleavage reaction.

The thermal cleavage of 1,2-dichloroethane to give hydrogen chloride and vinyl chloride is carried out industrially on a large scale. The process is described in, for example, Ullmanns Encyklopädie der technischen Chemie (Ullmann's Encyclopedia of Industrial Chemistry) 4th Edition (1975), Vol. 9, pages 447 and 448. According to this, the cleavage is carried out at 500 to 550° C., and conversions of about 50 to 60% are achieved. To increase the conversion and/or to reduce the cleavage temperature, it is possible to add so-called initiators, for example in amounts of from 0.2 to 0.5%. Initiators or catalysts of this type which are specified are chlorine, oxygen, iodine or carbon tetrachloride, but it is found that the addition of initiators of this type also increases the amounts of byproducts, for which reason this addition is dispensed with industrially. It can be seen from the same literature reference that 1,2-dichloropropane exerts a strongly inhibiting, which means adverse, effect on the thermal dehydrochlorination of 1,2-dichloroethane.

The preparation of vinyl chloride by thermal cleavage of dichloroethane under pressures between 3 and 20 atmospheres absolute (0.29 to 1.96 MPa) by heating at tempertures between 500° and 620° C. in the presence of 0.5 to 2% by weight of halogen or compounds eliminating halogen is disclosed in German Auslegeschrift No. 1,210,800. compounds eliminating halogen are to be understood to be sulfuryl chloride, thionyl chloride, hexachloroethane, carbon tetrachloride and perchloroethylene. Chlorine compounds are preferred, but chlorinated hydrocarbons having more than 2 carbon atoms should be avoided because of the resulting byproducts.

In addition, a process for the preparation of vinyl chloride by dehydorchlorination of dichloroethane by heating in the presence of an initiator is disclosed in German Offenlengungsschrift No. 1,953,240, the process being carried out at temperatures of from 250° to 450° C. under a pressure of from 2 to 30 atmospheres (0.19 to 2.94 MPa) in the presence of 0.2 to 0.9% by weight, relative to dichloroethane used, of an initiator. Initiators of this type which are mentioned are chlorine, oxygen, nitrosyl chloride or hexachloroethane.

Furthermore, the use as initiators for the thermal decomposition of 1,2-dichloroethane, under a pressure of from 20 to 35 atmospheres (2.02 to 3.64 MPa) and at a reaction temperature of from 450° to 650° C., of 0.005 to 1 mol-% of a compound of the general formula $CX_3NO_2$ (in which X represents H, Cl, Br, $CH_3$ or $NO_2$) is disclosed in Japanese Patent Application Sho No. 42-22921, published on Nov. 8, 1967.

Bromotrihalogenomethanes, for example $CCl_3Br$, and 1,2-dibromoethanes as initiators for the thermal decomposition of 1,2-dichloroethane are disclosed in Japanese Patents Sho No. 40-28779 and Sho No. 55-68834. Compared with chlorine and compounds containing chlorine, bromine and compounds containing bromine generally have the disadvantage that, at the high temperatures necessary for the decomposition of 1,2-dichloroethane, they are associated with considerable problems of corrosion, moreover they are more costly than the chlorine compounds. Sulfuryl chloride and thionyl chloride require additional elaboration of the work-up to remove the sulfur dioxide which is formed. The same applies to nitrosyl chloride and the methanes containing nitro groups, of the formula $CX_3NO_2$, which likewise require an increased elaboration of the work-up to remove the nitrogen oxides which are produced, moreover problems with exit gases can also appear in this case.

At variance with the statements in German Auslegeschrift No. 1,210,800, according to which chlorinated hydrocarbons having more than 2 carbon atoms should be avoided because of the occurrence of byproducts, it has been found that certain chlorinated hydrocarbons having 3 carbon atoms are very good initiators for the thermal decomposition of 1,2-dichloroethane, and the action of some of them is superior to the initiators containing chlorine and/or nitro groups hitherto mentioned in the state of the art. When applied to the same conversion of the 1,2-dichloroethane, they result in fewer undesired byproducts than is the case with, for example, the addition of a known chlorinated hydrocarbon initiator having 2 carbons atoms, or without the addition of any initiator. The good action of certain chlorinated hydrocarbons having 3 carbon atoms was surprising because other chlorinated hydrocarbons having 3 carbon atoms, for example 1,2-dichloropropane, have the reverse effect, acting as inhibitors of the thermal decomposition of 1,2-dichloroethane (see Ullmann Loc. cit.).

The object of the present invention is to make available a process which makes it possible to reduce the cleavage temperature for the thermal cleavage of 1,2-dichloroethane, and to produce fewer undesired byproducts during the cleavage.

This object is achieved by a process for the thermal cleavage of 1,2-dichloroethane to give vinyl chloride, at 300° to 600° C., under atmospheric pressure or elevated pressure, in the presence of at least one compound accelerating the cleavage reaction, which process comprises using as the compound(s) of this type 0.001 to 5% by weight, relative to 1,2-dichloroethane used, of trichloroacetyl chloride or a compound which contains 3 carbon atoms, at least 6 chlorine atoms, 0 or 1 oxygen atom and, for each carbon atom bonded to the latter, 0 or 1 hydrogen atom.

Apart from trichloroacetyl chloride, examples of suitable compounds are pentachloropropionyl chloride, hexachloroacetone and hexachloropropane. Particularly good results are obtained with hexachloropropene, heptachloropropane and octachloropropane. It is possible to use one of the compounds to be used according to the invention, or a mixture of several such compounds, as well as mixtures of the compounds to be used according to the invention with known compounds accelerating the cleavage reaction of 1,2-dichloroethane.

The compounds to be used according to the invention are advantageously added to the liquid 1,2-dichloroethane, which has been conventionally purified, before it is fed into the thermal decomposition. To improve the metering, it is advisable first to prepare a concentrated, approximately 30 to 60% by weight, solution of the compounds in the purified 1,2-dichloroethane, and to add this solution, using conventional metering equipment, for example a metering pump, to the main quantity of the purified 1,2-dichloroethane.

If less than 0.001% by weight, relative to 1,2-dichloroethane, of the compounds to be added according to the invention is used, then the accelerating action is no longer adequate. When more than 5% by weight, relative to 1,2-dichloroethane used, is added, the disadvantages, for example increased formation of byproducts and higher costs, outweigh the additional effects which can be achieved. Preferably, 0.005 to 1% by weight, relative to 1,2-dichloroethane used, is used. At comparatively low cleavage temperatures in the range from 350° to about 450° C., the quantities selected for addition will tend to be in the upper part of the preferred range, say between 0.2 and 1% by weight, while at higher cleavage temperatures, say in the range from 450° to 550° C., the quantities selected for addition will advantageously tend to be in the lower part of the preferred range, in particular from 0.005 to 0.1% by weight, relative to 1,2-dichloroethane used.

Below a cleavage temperature of 300° C., the compounds to be used according to the invention no longer lead to economically acceptable conversions. Above a cleavage temperature of 600° C., the process according to the invention no longer has sufficient advantages. It is preferably carried out in the temperature range from 350° to 550° C.

The mean dwell time of the gaseous 1,2-dichloroethane in the zone heated to the cleavage temperature can generally be 2 to 100 s, and, advantageously, lower dwell times are selected at higher cleavage temperatures (500° to 600° C.) than at lower cleavage temperatures (300° to 500° C). When the new process is carried out on the industrial scale, dwell times of from 4 to 40 s will be used.

The process according to the invention can be carried out under atmospheric pressure (0.0983 MPa). To increase the space-time yield in the cleavage furnace, it is advantageous to work under pressures up to about 5 MPa, preferably under pressures of 1 to 4 MPa.

The thermal cleavage of 1,2-dichloroethane with the addition according to the invention is carried out by conventional processes, for example in a known tubular cleavage furnace, in empty tubes of internal diameter from 20 to 160 mm, which are heated externally. After leaving the thermal cleavage, the hot cleavage gases are cooled conventionally, the hydrogen formed and the vinyl chloride, as well as the unreacted 1,2-dichloroethane, are separated by distillation and purified by conventional processes.

The process according to the invention can be used either to reduce the cleavage temperature at the same conversion or to increase the conversion at the same cleavage temperature. Particularly when the cleavage temperature is reduced, in addition to the saving in energy, a reduction in interfering byproducts is found. The process can be carried out in the available largescale industrial plants for the cleavage of 1,2-dichloroethane with little additional elaboration of equipment.

The examples and comparison tests which follow are intended to illustrate the invention in detail:

Comparison of various initiators for the thermal cleavage of 1,2-dichloroethane.

The apparatus used comprises a storage vessel for 1,2-dichloroethane, and a rotameter which is connected to a glass flask which can be heated and which in turn is connected to a quartz tube which has an internal diameter of 18 mm and can be heated for 500 mm of its length. The exit of the quartz tube is connected via a nonreturn valve to 4 wash bottles connected in series, downstream of which is a cold trap. The first wash bottle, viewed from the end of the quartz tube, contains distilled water, the second contains a 1 M potassium hydroxide solution in water, and the third and fourth wash bottles each contain 100 cm$^3$ of dimethyl glycol. The wash bottles filled with water and with potassium hydroxide solution are cooled to +5° C. The wash bottles containing dimethyl glycol are at about 20° C., and the cold trap connected thereto is cooled to −78° C. During each test, the glass flask is heated to 350° C., and the quartz tube is heated to 400° C. (measured on the outer wall of the tube in the center of the heating zone). The storage vessel is filled with 1,2-dichloroethane to which 1% by weight, in each case, of the initiators indicated in the table below have been added. 47.2 g of 1,2-dichloroethane per hour passes through the rotameter into the heated glass flask and are there vaporized. The vapors are passed through the quartz tube and the connected wash bottles and the cold trap. The test is stopped after 1 hour, the dimethyl glycol from the third and fourth wash bottles is combined with the 1,2-dichloroethane which has condensed in the first and second wash bottles, and the amount of vinyl chloride contained in the combined liquids is determined using quantitative gas chromatography. The result is verified by balancing the weights and back-titration of the potassium hydroxide solution which had been initially introduced. The values obtained are given in the table below in percent by weight relative to the theoretical amount of vinyl chloride to be expected when cleavage of 1,2-dichloroethane is 100% (=100% by weight). No condensate had formed in the cold trap. The dwell time of the vapors of 1,2-dichloroethane in the heated zone of the tube (calculated taking no account of the proportion of 1,2-dichloroethane cleaved) was about 17 s.

In all the tables below, the comparison tests according to the state of the art are identified by letters, and the examples according to the invention are identified by numbers.

| Comparison test or example | Nature of the addition | % by weight of vinyl chloride after cleavage | Notes |
| --- | --- | --- | --- |
| A | No addition | 0.3 | State of the art |
| B | Chlorine (Cl$_2$) | 4 | |
| C | Thionyl chloride (SOCl$_2$) | 10.2 | |
| D | Sulfuryl chloride (SO$_2$Cl$_2$) | 24.8 | |
| E | Nitromethane (CH$_3$NO$_2$) | 6.5 | |
| F | Nitrosyl chloride (NOCl) | 32.7 | |
| G | Tetrachloromethane (CCl$_4$) | 2 | |
| H | Hexachloroethane (C$_2$Cl$_6$) | 6.5 | |
| 1 | Trichloroacetyl chloride (CCl$_3$COCl) | 16 | According to the invention |
| 2 | Hexachloropropene (CCl$_3$CCl=CCl$_2$) | 42 | |
| 3 | Heptachloropropane (CCl$_3$CCL$_2$CHCl$_2$) | 62 | |
| 4 | Octachloropropane (C$_3$Cl$_8$) | 89 | |

Comparison tests I, K and L and Examples 5 and 6: The following apparatus is used: a storage vessel for 1,2-dichloroethane is connected via a rotameter to a glass flask which can be heated, and the latter in turn is connected to a quartz tube of internal diameter 6 mm, which can be heated for 500 mm of its length. At the end of the quartz tube, a wash bottle containing a 1 M potassium hydroxide solution in water at a temperature of 20° C. is connected via a non-return valve. The exit from the wash bottle is connected to a gas receiver. At the start of the tests, the quartz tube is heated to the particular temperatures indicated in Table II below (measured at the outer wall of the tube in the center of the heating zone). The glass flask is heated to 350° C. The storage vessel is filled with 1,2-dichloroethane containing, depending on the test, the amount of initiator indicated in Table II below. 68 g of 1,2-dichloroethane are passed continuously over the course of 3½ hours from the storage vessel via the rotameter into the heated glass flask, vaporized there, cleaved in the heated quartz tube, and then washed with potassium hydroxide solution, and the gases which have not condensed in the washer are collected in the gas receiver. After ending the test, the amount of gas present in the gas receiver is measured, and its composition is determined by gas chromatography. Likewise, the EDC condensate is weighed and subjected to quantitative analysis by gas chromatography. The conversion of the 1,2-dichloroethane is determined from these data. The area in the gas chromatogram, relative to the total area (=1 million), for a number of byproducts is determined, and the ppm areas thus determined are given in Table II below. the soot deposited in the quartz tube is determined by conventional combustion analysis, and is given in the table in mg (produce from incomplete thermal cleavage of 68 g of 1,2-dichloroethane in each case). The initiators used are hexachloroethane ($C_2Cl_6$) according to the state of the art and octachloropropane ($C_3Cl_8$) according to the invention.

| Comparison test/ Example | I | K | 5 | L | 6 |
|---|---|---|---|---|---|
| Nature of the initiator | — | $C_2Cl_6$ | $C_3Cl_8$ | $C_2Cl_6$ | $C_3Cl_8$ |
| Amount of the initiator (% by weight) | — | 0.01 | 0.01 | 1 | 1 |
| Temp. of the wall of the cleavage tube (°C.) | 580 | 550 | 530 | 450 | 350 |
| Conversion of 1,2-dichloroethane (% by wt.) | 53 | 52 | 52 | 56.5 | 58 |
| Byproducts ppm areas | | | | | |
| Ethane + ethene | 129 | 106 | 105 | 61 | 59 |
| Propene | 11 | 8.2 | 15 | 4 | 3.9 |
| Ethine | 625 | 557 | 478 | 533 | 371 |
| 1,3-butadiene | 30 | 25 | 21 | 13 | 15 |
| Chloromethane | 45 | 45 | 19 | 27 | 20 |
| But-1-n-3-ine | 48 | 33 | 29 | 33 | 12 |
| 1,1-dichloroethene | 128 | 53 | 50 | 65 | 33 |
| Soot (mg) | 2.22 | 1.01 | 0.93 | n.d. | n.d. |

(n.d. = not determined)

We claim:

1. A process for the thermal cleavage of 1,2-dichloroethane to give vinyl chloride, at 300° to 600° C., under atmospheric pressure or elevated pressure, in the presence of at least one compound accelerating the cleavage reaction, which comprises using as the compound(s) of this type 0.001 to 5% by weight, relative to 1,2-dichloroethane used, of a compound which consists of 3 carbons atoms, at least 6 chlorine atoms, 0 or 1 oxygen atom and, for each carbon atom bonded to the latter, 0 or 1 hydrogen atom.

2. The process as claimed in claim 1, which is carried out in the presence of 0.005 to 1% by weight, relative to 1,2-dichloroethane used, of at least one of the compounds, defined in claim 1, accelerating the cleavage reaction.

3. The process as claimed in claim 1, which is carried out in the presence of octachloropropane, heptachloropropane or hexachloropropene.

* * * * *